(12) United States Patent
Thatte et al.

(10) Patent No.: US 7,611,830 B2
(45) Date of Patent: Nov. 3, 2009

(54) DEVICE TO LAVAGE A BLOOD VESSEL

(75) Inventors: Hemant Thatte, Medfield, MA (US);
Kunda Biswas, Boston, MA (US);
Shukri Khuri, Westwood, MA (US);
Thomas Michel, Lincoln, MA (US)

(73) Assignee: The United States of America as represented by the Department of Veteran's Affairs, Washington, DC (US)

( * ) Notice: Subject to any disclaimer, the term of this patent is extended or adjusted under 35 U.S.C. 154(b) by 834 days.

(21) Appl. No.: 10/257,176

(22) PCT Filed: Apr. 10, 2001

(86) PCT No.: PCT/US01/11834

§ 371 (c)(1),
(2), (4) Date: Jul. 14, 2003

(87) PCT Pub. No.: WO01/76364

PCT Pub. Date: Oct. 18, 2001

(65) Prior Publication Data

US 2004/0102415 A1    May 27, 2004

Related U.S. Application Data

(63) Continuation-in-part of application No. 09/546,860, filed on Apr. 10, 2000, now Pat. No. 6,569,615.

(51) Int. Cl.
*A01N 1/00* (2006.01)
(52) U.S. Cl. .................... 435/1.1; 435/2; 604/1.01; 604/6.11; 600/36; 606/1; 623/916

(58) Field of Classification Search ............. 435/1.1, 435/2; 604/4.01, 6.11; 600/36; 623/916; 606/1
See application file for complete search history.

(56) References Cited

U.S. PATENT DOCUMENTS

| | | | | |
|---|---|---|---|---|
| 3,468,136 | A * | 9/1969 | Koski et al. | 62/64 |
| 3,995,444 | A * | 12/1976 | Clark et al. | 62/306 |
| 4,462,215 | A * | 7/1984 | Kuraoka et al. | 435/1.2 |
| 4,713,055 | A * | 12/1987 | Viggiano | 435/1.2 |
| 4,798,824 | A | 1/1989 | Belzer et al. | 514/60 |
| 5,070,085 | A | 12/1991 | Markham | 514/161 |
| 5,338,662 | A * | 8/1994 | Sadri | 435/284.1 |
| 5,407,793 | A | 4/1995 | Del Nido et al. | 435/1 |
| 5,514,536 | A | 5/1996 | Taylor | 435/1.2 |

(Continued)

OTHER PUBLICATIONS

Conklin, B.S., "Viability of Porcine Common Carotid Arteries i a Novel Organ Culture System," MS Thesis, Georgia Institute of□□Technology, 1997.*

(Continued)

*Primary Examiner*—Leon B Lankford
(74) *Attorney, Agent, or Firm*—Medlen & Carroll, LLP

(57) ABSTRACT

The present invention provides for compositions and methods for the preservation of tissues and organs ex vivo and in situ. In addition, the present invention provides for kits that may be used in the preparation of the solutions of the present invention. The present invention also provides a device for perfusing tissues and organs with the solutions of the present invention.

13 Claims, 7 Drawing Sheets

U.S. PATENT DOCUMENTS

| | | | | |
|---|---|---|---|---|
| 5,552,267 | A | | 9/1996 | Stern et al. ............... 435/1.1 |
| 5,599,659 | A | * | 2/1997 | Brasile et al. ............. 435/1.1 |
| 5,643,712 | A | | 7/1997 | Brasile ..................... 435/1.2 |
| 5,702,881 | A | | 12/1997 | Brasile et al. ............. 435/1.2 |
| 5,713,917 | A | * | 2/1998 | Leonhardt et al. ......... 606/194 |
| 5,786,136 | A | * | 7/1998 | Mayer ...................... 435/1.2 |
| 5,948,771 | A | | 9/1999 | Danziger ................... 514/185 |
| 6,100,082 | A | * | 8/2000 | Hassanein ................. 435/284.1 |
| 6,153,582 | A | | 11/2000 | Skelnik ..................... 514/12 |
| 6,322,553 | B1 | * | 11/2001 | Vito ......................... 606/1 |
| 6,567,679 | B1 | | 5/2003 | Treanor et al. ............. 600/345 |
| 6,600,941 | B1 | | 7/2003 | Khuri ....................... 600/345 |
| 6,899,669 | B2 | * | 5/2005 | Vito et al. .................. 600/36 |
| 7,011,623 | B2 | * | 3/2006 | Clerin et al. ................ 600/36 |

OTHER PUBLICATIONS

Calne et al., "Trickle perfusion for organ preservation," *Nature*, 235:171-173 (1972).

Hickethier et al., "Ultrastructural investigations for reducing endothelial cell damage of vein grafts during CABG-operation and practical consequences," *J Cardiovasc Surg*, 40:71-76 (1999).

Huk et al., "L-Arginine treatment alters the kinetics of nitric oxide and superoxide release and reduces ischemia/reperfusion injury in skeletal muscle," *Circulation*, 96:667-675 (1997).

Lapenna et al., "Blood cardioplegia reduces oxidant burden in the ischemic and reperfused human myocardium," *Ann Thorac Surg.* 57:1522-1525 (1994).

Maurer et al., "Comparison of UW and Collins solutions for preservationof the rat heart," *Transplantation Proceedings*, 22:548-550 (1990).

Okouchi et al., "Effectiveness of modified University of Wisconsin solution for heart preservation as assessed in heterotopic rat heart transplant model," *J Thorac Cardiovasc Surg*, 99:1104-1118 (1990).

Oshima et al., "Long-term heart preservation using a new portable hypothermic perfusion apparatus," *J Heart Lung Transplant*, 18:852-861 (1999).

Oz et al., "Novel preservation solution permits 24-hour preservation in rat and baboon cardiac transplant models," *Circulation*, 88[part 2]:291-297 (1993).

Rinia-Feenstra et al., "Functional properties of the saphenous vein harvested by minimally invasive techniques," *Ann Thorac Surg*, 69:1116-20 (2000).

Swanson et al., "Improved heart preservation with UW preservation solution," *J Heart Transplant*, 7:456-467 (1988).

* cited by examiner

Comparison of cell viability of human saphenous veins stored in HBSS vs GALA solution Cell viability of human saphenous vein following 24 hours of storage in GALA solution Human SVG Stored In Preservation Solutions For 3 Hours

DEVICE TO LAVAGE A BLOOD VESSEL

This application is a U.S. national entry of International Application No. PCT/US01/11834, filed Apr. 10, 2001, which is a continuation-in-part of U.S. application Ser. No. 09/546,860, filed Apr. 10, 2000, now U.S. Pat. No. 6,569,615.

The present invention was financed with government funds. The federal government has certain rights in this invention.

FIELD OF INVENTION

Generally, the present invention relates to the field of tissue preservation. In particular, the present invention relates to a solution for prolonged organ preservation, and more particularly to an aqueous salt solution for the preservation of grafts prior to transplantation. The invention also provides a method of preserving or maintaining an organ, comprising contacting the organ with an aqueous salt solution for organ preservation or maintenance.

BACKGROUND

Many different tissue and organ preservation solutions have been designed, as investigators have sought to lengthen the time that a tissue or organ may remain extra-corporeally, as well as to maximize function of the organ following implantation. Several of the key solutions that have been used over the years include: 1) the Stanford University solution [see, e.g., Swanson, D. K., et al., Journal of Heart Transplantation, (1988), vol. 7, No. 6, pages 456-467 (mentions composition of the Stanford University solution)]; 2) a modified Collins solution [see, e.g., Maurer, E. J., et al., Transplantation Proceedings, (1990), vol. 22, No. 2, pages 548-550; Swanson, D. K., et al., supra (mention composition of modified Collins solution)]; and 3) the University of Wisconsin solution (Belzer, et al., U.S. Pat. No. 4,798,824, issued Jan. 17, 1989). Of those, the University of Wisconsin (UW) solution is currently regarded as the best. (See, e.g., Maurer, E. J., et al., supra).

In addition to the composition of the tissue and organ preservation and maintenance solution, the method of tissue and organ preservation also affects the success of preservation. Several methods of cardiac preservation have been studied in numerous publications: 1) warm arrest/cold ischemia; 2) cold arrest/macroperfusion; 3) cold arrest/microperfusion; and 4) cold arrest/cold ischemia. The first method involves arresting the heart with a warm cardioplegic solution prior to exsanguination and cold preservation, but this method fails because of the rapid depletion of myocardial energy stores during the warm period The second method, which involves arresting the heart with a cold preservation solution, is better; but continuous perfusion of the heart with preservation solution during the storage period fails because of the generation of toxic oxygen radicals. In addition, the procedure of the second method is cumbersome and does not lend itself to easy clinical use. The third method, first described in the journal *Nature* in 1972 in a system called "trickle perfusion," is better but also cumbersome. The fourth method of preservation is that of a cold cardioplegic arrest followed by a period of cold immersion of the heart. The fourth method is currently the standard method of cardiac preservation. This fourth method reliably preserves hearts for periods of up to six (6) hours, but less than four (4) hours is considered ideal for this method. Since a longer preservation time is desirable, attempts have been made to improve preservation solutions in such a way as to reliably preserve hearts and other organs for longer periods of time.

Though the University of Wisconsin (UW) solution is currently the industry standard of organ preservation solutions, it is limited in the length of preservation time that it provides. Other solutions have been proposed (see, for example, U.S. Pat. No. 5,552,267 to Stern), however, these have limited use do to the complicated nature of the composition.

The relationship between the long-term patency and endothelial cell preservation has been established. Endothelial cells are known to be important mediators in regulating platelet, anticoagulant, procoagulant, and fibrinolytic functions. These activities of the endothelium allow for control of blood flow as well as thrombosis or blood clotting when there is endothelial injury. Presently, storage solutions are limited in the length of storage (up to 125 minutes) and protection provided to the endothelium. This time frame is insufficient depending on the type of operation being performed (i.e. whether or not a valve replacement or carotid endarterectomy will be needed along with bypass) and on the surgeon performing the operation.

Currently available storage solutions used during bypass surgery vary from normal saline, to physiological salt solutions, to heparinized blood. These solutions do not provide an adequate environment for endothelial or smooth muscle cell support. Normal saline lacks an energy source such as glucose. The pH of saline solutions tend to be low in the 6 to 7 range which is hostile to these fragile cells. Heparinized blood has only been shown to provide adequate storage of veins only up to 90 minutes. All of the currently available solutions are deficient in the combination of free radical scavengers, antioxidants, and nitric oxide synthase substrates that can provide a protective environment for cellular support during this time period where much damage occurs.

The saphenous vein is the most commonly used conduit for coronary artery bypass graft (CABG). The intraoperative preservation of harvested saphenous veins prior to performance of a CABG is believed to be a factor in the protection of the endothelial cells. Indeed, the relationship between the long-term patency and endothelial cell preservation is well established. That is to say, the preservation of endothelial cell viability is vital for inhibiting early pathological changes and the long-term patency of vascular grafts. Zilla P, von Oppell U, Deutsch M. The endothelium: A key to the future. J Card Surg 1993;8:32-60. Restenosis of venous bypass grafts, however, is a common sequelae proximal to vascular endothelial injury that occurs during vein harvest.

The pathological changes leading to ultimate vein graft occlusion and loss in vasomotor function are well documented. Verrier E D, Boyle E M. Endothelial cell injury in cardiovascular surgery: An overview. Ann Thorac Surg 1997; 64:S2-8. Endothelial damage appears to be a major cause of graft failure. Specifically, this injury may occur at the time of harvest due to blunt surgical trauma and stretch and due to distension or pressurization prior to anastomosis. Endothelial trauma is also caused by exposure to arterial circulation pressure and oxygenated blood after graft insertion.

Additionally, endothelium damaged or denuded saphenous veins are highly sensitive to the very potent, endothelium derived, circulating endogenous vasoconstrictors. For example, endothelin-1, $TXA_2$, and angiotensin II known to increase during CABG surgery. The increase in vascular tone mediated by these vasoconstrictors may lead to attenuated blood flow, stasis, and predisposition to thrombus formation in venous grafts.

What is needed is a physiological salt solution that would prolong the storage and protection available to harvested bypass conduits and other organs such as those used for transplantation in excess of 24 hours on the basis of cell viability and the integrity of key cell regulatory pathways, including nitric oxide synthesis. In addition devices and methods are also needed that precondition blood vessel grafts without damaging the endothelium of said blood vessels during perioperative graft preparation.

SUMMARY OF INVENTION

Generally, the present invention relates to the field of tissue preservation. In particular, the present invention relates to a solution for prolonged organ preservation, and more particularly to an aqueous salt solution for the preservation of grafts prior to transplantation. The invention also provides a method of preserving or maintaining an organ, comprising contacting the organ with as aqueous salt solution for organ preservation or maintenance.

Adequate preservation of organs intended for transplantation is critical to the proper functioning of the organ following implantation. This invention concerns an organ preservation or maintenance solution that can preserve organs intended for transplantation for periods of time that are longer than the currently best solution available. In particular, the present invention concerns the preservation of venous and arterial grafts. A longer preservation time is desired to enable cross-matching of donor and recipient to improve subsequent survival, as well as to allow for coast to coast and international transportation of organs to expand the donor and recipient pools. Experimental work for this invention has focused on the heart and heart tissues, but the organ preservation or maintenance solution of the subject invention may be used for other organs, and for tissues and cells, as well.

The organ preservation or maintenance solution of the present invention shows a substantial improvement over the prior art for increasing the preservation time for organs intended for transplantation. (See Experimental section). The organ preservation or maintenance solution of this subject invention shall be referred to as the GALA solution (named after Glutathione, Ascorbic acid, L-Arginine).

The present invention differs from other organ preservation solutions of the prior art in a number of respects. In our experiments, none of these solutions were able to preserve the structural integrity and function of saphenous vein endothelium for more than 2 hours. The present invention includes NOS substrates and antioxidants and is simple to prepare, being composed of a limited number of ingredients. Additionally, it does not require the elimination of sodium, calcium and chloride from the solution, as does at least one prior art solution (see U.S. Pat. No. 5,552,267 to Stem, et al.). In these regards, the present invention is improved over prior art compositions in that it permits the viability of tissue to be maintained longer than in traditional solutions and it is easier to prepare.

The GALA solution of the present invention is based on Hank's balanced saline solution. Hank's balanced salt solution (HBSS) is a commercially available physiological salt solution containing D-glucose 1 g/L, calcium chloride (anhydrous) 0.14 g/l, potassium chloride 0.4 g/l, potassium phosphate 0.06 g/l, magnesium chloride.$6H_2O$ 0.1 g/l, magnesium chloride.$7H_2O$ 0.1 g/l, sodium chloride 8 g/l, sodium bicarbonate 0.35 g/l, and sodium phosphate 0.048 g/l. The present invention modifies HBSS by the addition of ascorbic acid (vitamin C), reduced glutathione, L-arginine, and heparin to a final concentrations of about 500 μM, 1000 μM, 500 μM, and 50 Units/ml, respectively. The pH is then adjusted to 7.4 using 10 M sodium hydroxide. To date, no known preservation solution for harvested veins and arteries has been enhanced with ascorbic acid, glutathione, L-arginine, and heparin in an attempt to prevent endothelial injury. This new solution provides free radical scavengers, antioxidants, an NO substrate, a reducing agent, an energy source (glucose), an anti-coagulant, and physiological concentrations of electrolytes and buffers. As demonstrated in the Experimental section (below), the solution has the unexpected benefit of providing a greatly extended preservation time over the available prior art preservation solutions.

The present invention is not limited to the compositions listed above. Adenosine may be added as a supplemental energy source. Adenosine may be added a concentration of about 500 μM-5000 μM. Additionally, Lacidipine, a vasorelaxant calcium channel blocker, may be added to GALA in the final concentration of about 1 pM-1 mM. Additionally still, vasoactive intestinal peptide (VIP) may be added to GALA in the final concentration of about 1 μM-1 mM. Additionally still, Endothelin receptor agonists/antagonists (ETa and Ebb-receptors) may be added to GALA. Although the present invention is not limited to any particular mechanism, endothelin receptor agonists/antagonists work as vasocontractors and vasorelaxants, respectively. Furthermore, an anticoagulant need not be added, for example, in situations where the tissue or organ has been perfused of blood. Further still, glutathione need not be added because, for example, it is partly synergistic with ascorbic acid. Therefore, it is contemplated that a minimal formulation of the present invention would be HBSS with ascorbic acid and L-arginine added in to the concentrations listed above.

The present invention is not limited to any particular concentration of the ingredients listed above. In one embodiment, the concentration of ascorbic acid is between about 25-1000 μM. In another embodiment, the concentration of glutathione is between about 50-2000 μM. In yet another embodiment, the concentration of L-arginine is between about 250-2000 1μM. In still yet another embodiment, the concentration of heparin is between about 50-250 units/l. The present invention is not limited to any particular pH. In one embodiment the pH of the solution is between about pH 6.6-8.0. More preferably, the pH is between about pH 7.0-7.6. The present invention is not limited to any particular anticoagulant. In one embodiment, the anticoagulant is heparin. In another embodiment the anticoagulant is hirudin. The solution of the present invention may contain certain bacteriostats. The bacteriostat may be selected from a group comprising penicillin and cerfazolin. Other bacteriostats may be used. Selection of a bacteriostat may be determined at the time of practicing the invention. For example, allergies may be taken into account when selecting a bacteriostat.

The solutions, devices, and perfusion methods of the present invention are not limited to use with a particular tissue, organ or cell type. For example, the invention may be used with harvested saphenous veins, epigastric arteries, gastroepiploic arteries and radial arteries used in coronary bypass grafting (CABG). The present invention may also be used to maintain organs and tissue during transplant operations. The present invention is not limited to any particular tissue or organ. For example, it is contemplated that such organs or tissues may be heart, lungs, kidney, brain, muscle grafts, skin, intestine, bone, appendages, eyes, etc or portions thereof. Additionally, the present invention may be used as an in situ tissue or organ preservative. It is contemplated that the solution of the present invention be used to wash and bath tissues and organs that have not been removed from the patient. For example, it is contemplated that the present invention be used during cardioplegia. It is also contemplated that the present invention be used in, for example, emergency procedures where a tissue or organ may need to be bathed to preserve it until surgery or other medical attention can be obtained. In this regard, the solution may be made available to emergency medical personnel both in hospital settings and "in the field" (i.e., in ambulances or in temporary emergency medical facilities).

The present invention contemplates the present invention may be an aqueous solution or the present invention may be composed of powders and concentrated solutions that could be mixed with sterile water, as needed. The present invention also contemplates that the invention may be composed of a quantity of HBSS along with a supplement package that may be mixed with the HBSS.

The present invention contemplates an aqueous solution for organ and tissue preservation, comprising: a) calcium ions; b) D-glucose (from about 50 mM to about 120 mM); c) potassium ions (from about 100 mM to about 250 mM; derived from compounds selected from the group consisting of potassium chloride, and potassium phosphate); d) magnesium ions (from about 2 mM to about 20 mM; derived from compounds selected from the group consisting of magnesium sulfate, and magnesium chloride); e) sodium ions; f) ascorbic acid in a concentration of about 25-1000 µM; g) glutathione in a concentration of about 50-2000 µM; h) L-arginine in a concentration of about 250-2000 µM; i) an anticoagulant (selected from heparin and hirudin) at a concentration sufficient to substantially inhibit blood coagulation (for heparin this would be from about 50 units/l to about 250 units/l); and j) a buffer (the buffer is selected from the group consisting of sodium phosphate and sodium bicarbonate) in an amount sufficient to maintain the pH of said aqueous organ preservation solution at about 6.8 to 8.0.

The present invention contemplates an aqueous solution for organ and tissue preservation, comprising: a) calcium ions; b) D-glucose (from about 50 mM to about 120 mM); c) potassium ions (from about 100 mM to about 250 mM; derived from compounds selected from the group consisting of potassium chloride, and potassium phosphate); d) magnesium ions (from about 2 mM to about 20 mM; derived from compounds selected from the group consisting of magnesium sulfate, and magnesium chloride); e) sodium ions; f) ascorbic acid in a concentration of about 25-1000 µM;
  g) glutathione in a concentration of about 50-2000 µM; h) L-arginine in a concentration of about 250-2000 µM; i) an anticoagulant (selected from heparin and hirudin) at a concentration sufficient to substantially inhibit blood coagulation (for heparin this would be from about 50 units/l to about 250 units/l); and j) a buffer (the buffer is selected from the group consisting of sodium phosphate and sodium bicarbonate) in an amount sufficient to maintain the pH of said aqueous organ preservation solution at about 6.8 to 8.0; and k) tissue. Additionally, the present invention contemplates that the tissue is saphenous vein.

The present invention contemplates a method for preserving tissue comprising:
  i. providing a tissue; ii. contacting said tissue with a solution comprising: a) calcium ions in an amount sufficient to support intracellular function and maintenance of cellular bioenergetics; b) D-glucose in an amount sufficient to support intracellular function and maintenance of cellular bioenergetics; c) potassium ions in an amount sufficient to support intracellular function and maintenance of cellular bioenergetics; d) magnesium ions in an amount sufficient to support intracellular function and maintenance of cellular bioenergetics; e) sodium ions in an amount sufficient to support intracellular function and maintenance of cellular bioenergetics; f) ascorbic acid in a concentration of about 25-1000 µM; g) glutathione in a concentration of about 50-2000 µM; h) L-arginine in a concentration of about 250-2000 µM; i) an anticoagulant at a concentration sufficient to substantially inhibit blood coagulation; and f) a buffer in an amount sufficient to maintain the average pH of said aqueous organ preservation solution at about a physiological ph or above.

Additionally, the present invention contemplates a kit for the preparation of an organ preservation solution comprising: i. a container; ii. an aqueous solution disposed within said container wherein said solution comprises; a) D-glucose; b) calcium chloride; c) potassium chloride; d) potassium phosphate; e) magnesium chloride 6.H$_2$O; f) magnesium chloride 7.H$_2$O; g) sodium chloride; h) sodium bicarbonate; and i) sodium phosphate; iii. a supplement for introduction into said solution comprising; j) ascorbic acid; k) glutathione; 1) L-arginine; and m) heparin.

Furthermore, the present invention contemplates a kit for the preparation of an organ preservation solution comprising: i. a container; ii. reagents deposited in said container, said reagents comprising, a) D-glucose; b) calcium chloride; c) potassium chloride; d) potassium phosphate; e) magnesium chloride 6.H$_2$O; f) magnesium chloride 7.H$_2$O; g) sodium chloride; h) sodium bicarbonate; and i) sodium phosphate; j) ascorbic acid; k) glutathione; l) L-arginine; m) heparin; and n) sterile water.

The present invention contemplates a composition comprising an aqueous salt solution comprising an antioxidant, glutathione, an L-amino acid and an anticoagulant. Additionally, the present invention contemplates the composition wherein it also comprises isolated tissue. Particularly, the isolated tissue may be a vein, and more particularly, a saphenous vein.

The composition of the present invention may also comprise glucose. Furthermore, the antioxidant of the present invention may be ascorbic acid. Yet further still, the concentration of the ascorbic acid is about 25-1000 µM. Even further still, the concentration of the glutathione is of about 50-2000 u. Even further still, the L-amino acid is L-arginine. Even further still, the L-arginine is present in a concentration of about 250-2000 u. Even further still, the anticoagulant is selected from the group consisting of heparin and hirudin. Even further still, the anticoagulant is heparin, and wherein said heparin is present in a concentration of between about 50 units/ml and about 250 units/ml.

The present invention contemplates a composition comprising an isolated tissue in an aqueous salt solution comprising an antioxidant, glutathione, an L-amino acid and an anticoagulant. Further still, the tissue is an isolated vein. Even further still, the vein is a saphenous vein. Even further still, the antioxidant is ascorbic acid and the ascorbic acid is present in a concentration of about 25-1000 u. Even further still, the glutathione is present in a concentration of about 50-2000 u. Even further still, the L-amino acid is L-arginine and is present in a concentration of about 250-2000 u. Even further still, the anticoagulant is selected from the group consisting of heparin and hirudin. Even further still, the anticoagulant is heparin, and wherein said heparin is present in a concentration of between about 50 units/ml and about 250 units/ml.

The present invention contemplates a composition comprising an isolated human tissue in an aqueous salt solution comprising an antioxidant, glutathione, an L-amino acid and an anticoagulant. Further still, the tissue is an isolated human vein. Even further still, the vein is a saphenous vein. Even further still, the antioxidant is ascorbic acid and the ascorbic acid is present in a concentration of about 25-1000 u. Even further still, the glutathione is present in a concentration of about 50-2000 u. Even further still, the L-amino acid is L-arginine and is present in a concentration of about 250-2000 u. Even further still, the anticoagulant is selected from the group consisting of heparin and hirudin. Even further still, the anticoagulant is heparin, and wherein said heparin is present in a concentration of between about 50 units/ml and about 250 units/ml.

The present invention contemplates a method, comprising: a) providing i) an isolated tissue and ii) an aqueous salt solution comprising an antioxidant, glutathione, an L-amino acid and an anticoagulant; and b) contacting said isolated tissue with said aqueous salt solution. Furthermore, the tissue is an isolated vein. Even further still, the is a saphenous vein. Even further still, the antioxidant is ascorbic acid and the ascorbic acid is present in a concentration of about 25-1000 u. Even further still, the glutathione is present in a concentration of about 50-2000 u. Even further still, the L-amino acid is L-arginine and is present in a concentration of about 250-2000 u. Even further still, the anticoagulant is selected from the group consisting of heparin and hirudin. Even further still, the anticoagulant is heparin, and wherein said heparin is present in a concentration of between about 50 units/mL and about 250 units/mL.

The present invention also contemplates devices and methods for perfusing tissues and organs, and in particular blood vessels and portions thereof. In one embodiment, the present invention contemplates a device, said device comprising, an incomplete, hollow circuit defining a liquid flow path in fluidic communication with a chamber, said incomplete circuit comprising a pump operably linked to pressure transducer (or sensor), said circuit terminating at first and second attachment points, said first and said second attachment points configured to accept a (substantially hollow) blood vessel (or segment thereof) having first and second ends, such that attachment of said first end of said blood vessel to said first attachment point and said second end of said blood vessel to said second attachment point generates a complete, hollow circuit defining a liquid flow path (thereby permitting the circulation of liquid through said circuit and said vessel).

It is not intended that the present invention be limited to the precise design of the first and second attachment points. It is only important that they be designed so as to permit attachment of tissues, such as vessels and segments thereof. In one embodiment, said first attachment point comprises a serrated nozzle. In a preferred embodiment, second attachment point comprises an adjustable serrated nozzle.

Since the present invention contemplates using human tissue in connection with said device, it is preferred that said chamber is sterile. Moreover, to avoid contamination, it is preferred that said chamber is disposable.

It is not intended that the present invention be limited to the nature of the material from which the hollow circuit of the device is fabricated. In one embodiment, said incomplete, hollow circuit is fabricated from a polymer. A convenient source of material for the circuit is tubing.

A variety of configurations for the circuit are possible and the present invention is not limited to circular flow paths. To be a "circuit" it is only necessary that a flow path for fluid be defined such that a complete traversal of which without local change of direction requires returning to the starting point. Of course, where the circuit is "imcomplete," it is not possible to return to the starting point; however, where the circuit is "complete" (e.g. completed by the attachment of a vessel or segment thereof), at least a portion of the liquid traversing the circuit will return to the starting point on the flow path. A "complete" circuit is largely "closed" in order to preserve the amount or level of liquid in the circuit. However, the present invention permits the circuit to be in liquid communication with both a reservoir and a chamber. The reservoir provides a source of liquid (e.g. aqueous salt solution). The chamber, when filled with liquid, allows for the "bathing" of the tissue or vessel on the outside, while the tissue or vessel (through the connection to the circuit) is perfused on the inside. Where tubing is used, said tubing may terminate either outside, inside or at the edge of said chamber, so as to define said first and second attachment points.

In an alternative embodiment, the device can comprise a "complete" circuit wherein a segment of the circuit (e.g. a segment of the tubing) is removable. In such an embodiment, the removable segment is removed and replaced with the tissue or vessel. In yet another embodiment, the circuit is "complete" and comprises extension points which allows for the attachment of a vessel (or portion thereof) so as to extend the circuit (or create a second circuit). In such an embodiment, liquid can circulate through the complete circuit or through the extended (or second) circuit.

The device of the present invention can be used with a variety of tissues and methods. In one embodiment, the method comprises a) providing i) a device comprising, an incomplete, hollow circuit defining a liquid flow path in fluidic communication with a chamber, said incomplete circuit comprising a pump operably linked to pressure transducer (or sensor), said circuit terminating at first and second attachment points, said first and said second attachment points configured to accept a blood vessel having first and second ends; and ii) a segment of a blood vessel, said blood vessel having a first end and a second end; and b) attaching, in any order, said first end of said segment to said first attachment point and said second end of said segment to said second attachment point, under conditions such that a complete, hollow circuit defining a liquid flow path is produced. In a preferred embodiment, the method further comprises, after step b, circulating an aqueous solution in said hollow circuit. In such an embodiment, a variety of solutions can be used; however, in a preferred embodiment, said aqueous solution comprises an antioxidant and L-arginine and may (optionally) further comprises an anticoagulant. and a cellular reducing agent.

The methods and devices described above can be used with a variety of tissues, organs and vessels. In one embodiment, a blood vessel is used, such as an isolated vein (e.g. a saphenous vein)

DEFINITIONS

Figure 1:
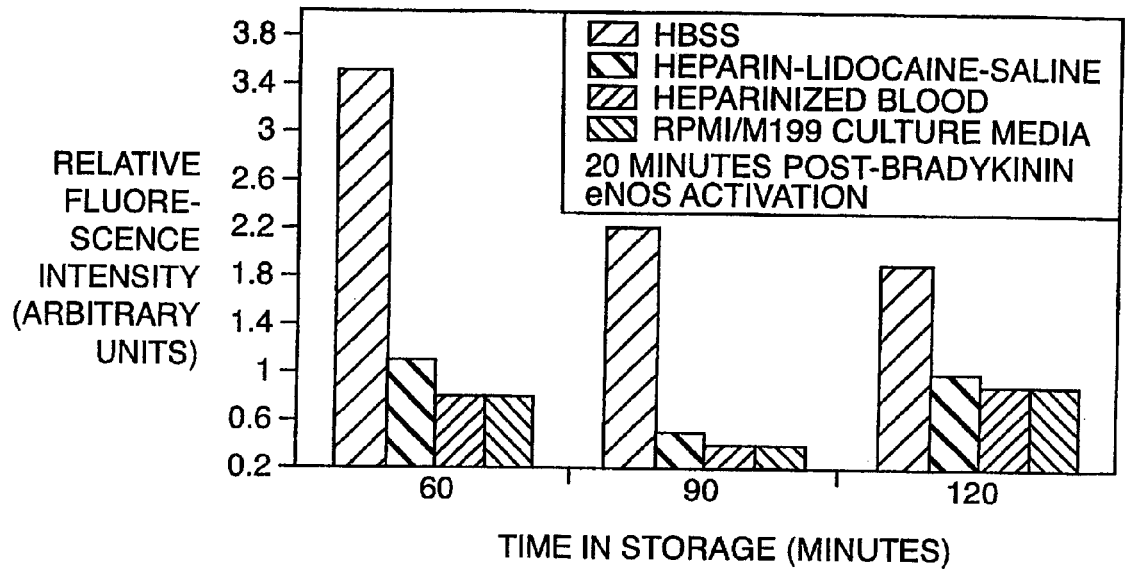
FIG. 1 shows the viability of human saphenous vein stored in various storage solutions.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, the term "patient" includes members of the animal kingdom including but not limited to human beings.

As employed herein, "organ" includes, but is not limited to, the heart, veins, arteries, lungs, liver, pancreas and the kidneys. Portions of organs are also contemplated.

As used herein, "sterile water" includes, but is not limited to, (a) sterile water for injection, USP, (b) sterile distilled deionized water, and (c) sterile water for irrigation.

As used herein, "cardioplegia" includes, but is not limited to, paralysis of the heart.

As used herein, "moderate hypothermia" is about 10°-21° C.

As used herein, an "antioxidant" is a substance that, when present in a mixture or structure containing an oxidizable substrate biological molecule, delays or prevents oxidation of the substrate biological molecule. For example, ascorbic acid is an antioxidant.

"Balanced salt solution" is defined as an aqueous solution that is osmotically balanced to prevent acute cell or tissue damage.

"Buffered salt solution" is defined as a balanced salt solution to which chemicals have been added to maintain a predetermined physiological pH range.

"Graft" is defined as tissue that is transplanted or implanted in a part of the body to repair a defect.

"Harvested bypass conduit" is defined as a surgically installed alternate route for the blood to bypass an obstruction.

"Solution of cardioplegia" is defined as a solution that aids in the preservation of the heart during transport or surgery.

"Cellular reducing agent" is defined as an a substance that loses electrons easily thereby causing other substances to be reduced chemically.

"Physiological solution" is defined as an aqueous salt solution which is compatible with normal tissue, by virtue of being isotonic with normal interstitial fluid.

DESCRIPTION OF DETAILED EMBODIMENTS

Generally, the present invention relates to the field of tissue preservation. In particular, the present invention relates to a solution for prolonged organ preservation, and more particularly to an aqueous salt solution for the preservation of grafts prior to transplantation. The invention also provides a method of preserving or maintaining an organ, comprising contacting the organ with as aqueous salt solution for organ preservation or maintenance. As such, the present invention is a novel solution that greatly increases the length of time the tissue or organ may remain out of the body. In addition, the present invention also presents a perfusion apparatus and methods of perfusion, which reduce endothelial damage to harvested tissues.

The organ preservation or maintenance solution may further comprise a reducing agent in an amount sufficient to help decrease reperfusion injury secondary to oxygen free radicals. The role of glutathione as a cellular reducing agent and L-arginine as the substrate for nitric oxide synthase has been well established. Studies have shown that the oral administration of a glutathione substrate improved endothelial dependent blood flow in patients with coronary artery disease.

The organ preservation or maintenance solution may further comprise an antioxidant in an amount sufficient to help decrease reperfusion injury secondary to oxygen free radicals. The antioxidant is selected from the group consisting of butylated hydroxyanisole (BHA), butylated hydroxytoluene (BHT), Vitamin C (ascorbic acid), Vitamin E, or suitable combinations thereof. Other suitable antioxidants may be used. In a preferred embodiment, the antioxidant is butylated hydroxyanisole (BHA) at a concentration range from about 25 microM to about 100 microM, alone or in combination with butylated hydroxytoluene (BHT) at a concentration range from about 25 microM to about 100 microM.

Currently, the protective role of ascorbic acid on endothelial cells is being investigated. Ascorbic acid is known to reduce platelet activation and leukocyte adhesion which are important events in the development of atherosclerosis. Ascorbic acid is also thought to contribute to the reduction in smooth muscle proliferation which is a key component of vein graft failure. Work by Jones and colleagues examined the protective effect of ascorbic acid by showing decreased adherence of neutrophils to the endothelium and free radical scavenging in human umbilical vein endothelial cells (HUVEC). Utoguchi and colleagues showed a decrease in endothelial layer permeability via ascorbic acid-mediated collagen synthesis in HUVEC monolayers. Adams and colleagues observed similar reductions in neutrophil-endothelial cell interactions after oral administration of L-arginine in cigarette smokers.

The organ preservation or maintenance solution may further comprise an anticoagulant in an amount sufficient to help prevent clotting of blood within the capillary bed of the organ. The anticoagulant is selected from the group consisting of heparin or hirudin. Other suitable anticoagulants may be used. In a preferred embodiment, the concentration of heparin ranges from about 50 units/l to about 250 units/l.

Anticoagulants are believed to help in preventing clotting of blood within the capillary bed of the preserved organ. Specifically, anticoagulants are believed to help prevent a total organ no-reflow phenomenon at the level of the microcirculation, which would be undesirable following re-implantation and could result in graft failure. Anticoagulants are believed to be helpful in ensuring that thrombosis does not occur during or after preservation, so that nutrient delivery and toxin removal can proceed.

The present invention contemplates a solution for tissue and organ preservation that is superior to prior art solutions in both the length of time it is able to preserve the tissue or organ, and in its ease of preparation. In one embodiment, the solution is based on HBSS. However, other solutions may be utilized as the basis of the tissue and organ preservation solution of the present invention. Any balanced saline solution could be used. For example, phosphate buffered saline, Ringer's solution, culture medias and cardiopelgic solutions could be used.

The present invention may be used as a cardioplegic solution. In this regard, the present solution would be administered to the patient's chest cavity after the heart was paralyzed by, for example, an injection of a potassium enriched solution. After the heart has depolarized, the chest cavity would be flooded with the solution of the present invention, or with an available cardioplegic solution with added glutathione, L-arginine, heparin and ascorbic acid. Additionally, the potassium concentration would be monitored and supplemented as necessary to maintain cardioplegia In another embodiment, the present invention provides a solution for cardioplegia during cardiac surgery and a solution for preserving a patient's heart for transplantation. Cardioplegia involves arresting the patient's heart or harvesting the patient's organ, perfusing the heart or organ with an aqueous solution of the present invention, and removing at least a substantial portion of the solution from the heart or organ to effect the removal of waste products from the heart or organ. Additionally, the present may be used for tissue and organ preservation for organs that are still within the patient's body or for tissues and organs that have been removed (for example, for transplantation). In this regard, the present invention may be used as a storage solution after removal of the tissue or organ or as a transportation solution for organs that need to be transferred to a new location for the transplantation to take place (for example, for transport of a heart, kidney or liver from a donor to a recipient). The present invention makes the transport of organs over much longer distances than can presently be accomplished.

Experimental

Suppliers

Live-Dead assay kit (calcein AM/ethidium homodimer) was obtained from Molecular Probes, Eugen, Oreg. Membrane permeable 4,5-diaminofluorescein diacetate (DAF-2/DA) was purchased from Calbiochem, La Jolla, Calif. Hank's balanced salt solution (HBSS), Minimum essential medium (MEM) and RPMI 1640 medium were obtained from Gibco-BRL, Grand Island, N.Y. HLS solution (heparin, 40 units/ml; lidocain, 0.0016%; saline, 0.9% NaCl) was from the Clinical Pharmacy at VA Medical Center, West Roxbury, Mass. L-arginine, reduced glutathione, L-ascorbic acid, bradykinin and $N^w$-nitro-L-arginine (LNNA) were purchased from Sigma Chemical Co., St. Louis, Mo. Specially designed chambers used for inverted microscopy consisting of a sterile 35 mm petri plate with a No. 1.5 coverslip sealed over a 10 mm hole in the bottom of the petri plate were obtained from MetTek Corp., Ashland, Mass. Pumps suited to the claimed perfusion device include, but are not limited to, Perimatic programmable peristaltic pump, catlog no. HX20722. Varistaltic Pump/Dispenser, catalog no. HX 20721. Fisherbrand-Variable-Flow Peristaltic pumps, catalog no. 13-876-2. Watson-Marlow PumpPro Variable speed transfer pump, catalog no. 144-283-2. Tubing suited to the perfusion circuit described in the present invention may be obtained from Fisher Scientific and Watson-Marlow.

EXAMPLE 1

Hank's balanced salt solution (HBSS), a commercially available physiological salt solution (Gibco/BRL, Grand Island, N.Y.) containing D-glucose 1 g/L, calcium chloride (anhydrous) 0.14 g/l, potassium chloride 0.4 g/l, potassium phosphate 0.06 g/l, magnesium chloride.$6H_2O$ 0.1 g/l, magnesium chloride.$7H_2O$ 0.1 g/l sodium chloride 8 g/l, sodium bicarbonate 0.35 g/l, and sodium phosphate 0.048 g/l was modified by the addition of ascorbic acid (vitamin C), reduced glutathione, L-arginine, and heparin to a final concentration of 500 µM, 1000 µM, 500 µM, and 50 Units/ml, respectively. The pH was then adjusted to 7.4 using 10 M sodium hydroxide. To date, no known preservation solution for harvested veins and arteries has been enhanced with ascorbic acid, glutathione, L-arginine, and heparin in an attempt to prevent endothelial injury. This new solution (known as GALA solution named after Glutathione, Ascorbic acid, L-Arginine) provides free radical scavengers, antioxidants, an NO substrate, a reducing agent, an energy source (glucose), an anti-coagulant, and physiological concentrations of electrolytes and buffers.

After approval from the Human Studies Subcommittee, discarded segments of saphenous veins used as bypass conduits were obtained from the operating room and transported to the laboratory for experimental work. Human saphenous veins (SVG) were excised and obtained from male patients undergoing cardiac bypass surgery at the West Roxbury Va. Medical Center, according to the protocol established by the scientific evaluation committee at the VA Medical Center. A 100 mm segment of 11.5 mm diameter was excised from the SVG or its branch in the operating room and immediately transferred to a storage solution maintained at 21° C. The vessel was transported to the Multi-photon microscopy laboratory in the Imaging Core facility of the West Roxbury Va. Medical Center for further processing, within 10 min after removal of the vessel from the patient. The vessel was minimally disturbed to protect it from blunt trauma during handling and processing. Excess adipose and adventitia were gently excised and the vessel was washed of any excess blood with the storage solutions under investigation. Prior to the assays, 8 mm segment of the vessel was cut as required and immediately transferred to the assay solution for further incubation. The rest of the vessel was maintained at 21° C. in the assay solution under similar conditions as those utilized in the OR during bypass surgery. In the initial set of experiments, four conventional types of storage solutions were studied for their protective effects on the saphenous veins in short-term storage. Vein segments were initially exposed to 60, 90, and 120 minutes of storage at 21° C. in either: 1) heparin-lidocaine-saline (HLS solution) containing 200 ml of 0.9% saline, 50 units/ml of heparin, and 40 ml of 1% lidocaine, 2) autologous blood with heparin 50 U/ml, 3) HBSS with heparin 50 U/ml or 4) RPMI/M199 culture medium in a 1:1 mixture with heparin 50 U/ml added.

To study the protective effects of GALA solution during prolonged storage conditions, experiments were performed using segments of saphenous vein exposed to 1-5 hours of at room temperature (21° C.). Control experiments were performed using HBSS as the storage solution for the same 5-hour exposures. To study the effects of overnight storage, vein segments were exposed to an additional 19 hours of storage at 4° C. in GALA solution prior to performance of viability and functionality assays.

Cell viability was measured using calcein-dependent green fluorescence and cell death was measured using ethidium homodimer-mediated red fluorescence. Following the appropriate exposures to the storage solutions, the veins were then incubated in a 15 µM solution of calcein/ethidium homodimer for 30 minutes at 21° C. for loading of the fluorophores. Imaging of vein segments was performed using the BioRad MRC 1024 ES multi-photon (MPM) imaging system coupled with a mode-locked Spectra-Physics tunable Tsunami titanium/sapphire laser system tuned to 790 nm (pulse duration<80 fs, repetition rate 82 MHz) and a Zeiss Axiovert S100 inverted microscope equipped with a high-quality immersion 40×/1.2 NA objective. The structural/functional viability of the saphenous veins was measured at 40× and/or 80×(zoom) magnification. The lumen and endothelial cell layers were identified by XYZ scanning at depths ranging from 30-200 µm. Data was expressed as percentage of living to dead cells. A viability score was derived based on the percentage of viable cells to non-viable cells and assigned for each storage solution.

Functionality of the veins was assessed by measuring the generation of NO induced by bradykinin (10 μM) activation of endothelial nitric oxide synthase (egos), the enzyme responsible for NO synthesis from L-arginine. The exposures to the storage solutions were performed in the same manner as in the viability studies at room temperature, and an additional 19 hours of storage at 4° C. The endothelial cells were labeled by incubating with 15 μM diaminoflurescein (DAF) in HBSS for 60 min at 37° C. DAF is a cell permeable NO fluorophore that fluoresces upon reaction with intracellularly-generated NO. The temporal increase in DAF fluorescence due to generation of NO was measured for 20 minutes using quantitative MPM imaging and BioRad LaserSharp software. In quantitating relative NO fluorescence, boundaries were drawn along the endothelial layer in 2 or 3 regions of the vessel lumens. Changes in the integrated fluorescence intensities over all pixels within the boundaries of each region were measured. The morphology of the region varied in terms of size and shape. As a result, the fluorescence intensities quantitated from each image were normalized to the reference image recorded prior to bradykinin activation. The data were expressed as a change in relative fluorescence intensity in reference to the pre-bradykinin non-stimulated image.

As a measure of endothelial cell functionality, egos activity was quantitated using bradykinin as the enzyme agonist. FIG. 1 depicts the results after storing vein segments in either Hank's balanced salt solution (HBSS), heparin-lidocaine-saline solution (HLS), heparinized blood, or a 1:1 mixture of RPMI and M199 culture media. A marked decrease in egos activity was noted following 90 and 120 minutes of storage. HBSS was superior to all other solutions in the initial set of experiments.

EXAMPLE 2

Figure 2:
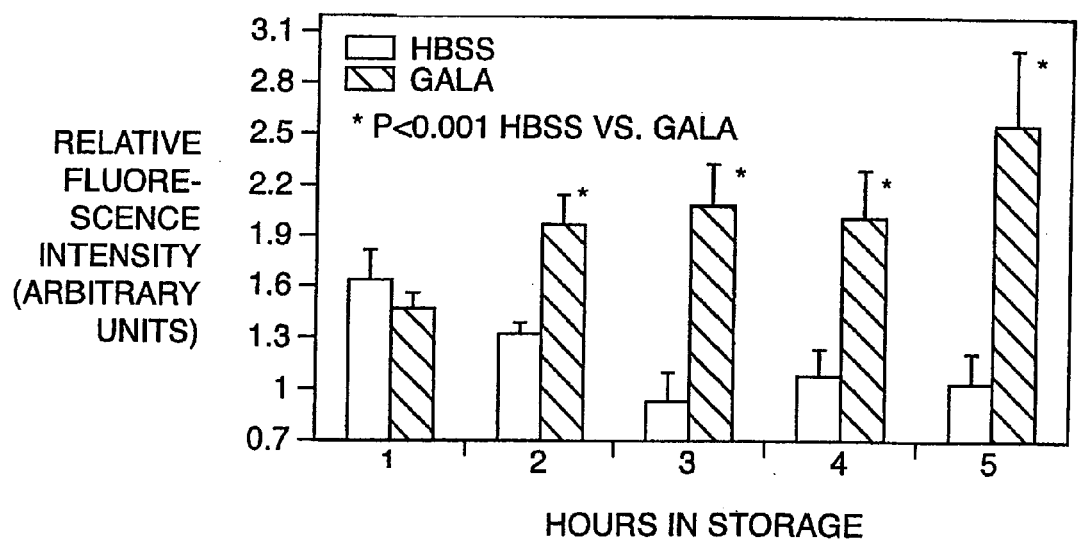
FIG. 2 shows the effects on endothelial nitric oxide synthase (egos) activity after 5 hours of storage in HBSS v. GALA solution.

We next sought to improve further on the composition of HBSS by adding compounds with theoretical value in sustaining endothelial cell viability and cellular function. The end result was the GALA solution. An evaluation of the ability of HBSS and GALA solution to protect the endothelial cells during prolonged storage was then undertaken. The other three types of storage media were not tested under these prolonged conditions due to the lack of predicted egos activity and viability. FIG. 2 shows the effects on egos activity after 5 hours of storage in HBSS v. GALA solution. Very little activity was noted in cells stored for 3, 4, and 5-hour exposures as compared to the 1 and 2 hour exposures for HBSS. In marked contrast, egos activity is sustained even after storage in GALA solution for up to 5 hours. The addition of ascorbic acid, glutathione, and L-arginine substantially prolonged the protection and functionality of the endothelial cells compared to the conventional HBSS solution ($P<0.001$ for egos activity of HBSS v. GALA for the 2, 3, 4, and 5-hour exposures).

Endothelial cell viability was also measured for the various storage solutions. Cells and tissues were observed as follows. BioRad MRC 1024ES multi-photon imaging system was coupled with a mode-locked Spectra-Physics tunable Tsunami Titanium/Sapphire laser system tuned to 790 nm, (pulse duration <80 fs, repetition rate 82 MH) and a Zeiss Axiovert S100 inverted microscope equipped with a high quality water immersion 40×/1.2 NA, C-apochroma objective was used to image the SVG at 40× and/or 80×(Zoom) magnification. The vessel lumen and the endothelial cell layer were identified by XYZ scanning and were generally at depths of 100-200 μ depending on the size of the vessel. The scan parameters are chosen such that 512×512 pixel images are generated with pixel residence time of 0.413 μsec. The images were reconstructed using the BioRad Laser Sharp software.

Table 1 lists the viability scores of the five storage solutions examined. In the Live-Dead assay, cells were considered living and/or dead when green and/or red fluorescence was observed, respectively. The vessel endothelium viability results were quantitatively expressed on a scale of 1-4. 4+ indicates a structurally intact endothelial layer, in contrast, 1+ score shows a compromised endothelial layer.

TABLE 1

Cell viability scores for the tested storage solutions.

| Solution | 60 min | 90 min | 120 min | 150 min | 180 min | 240 min | 300 min | 1440 min |
|---|---|---|---|---|---|---|---|---|
| HLS | + | + | NT | NT | NT | NT | NT | NT |
| Blood | + | + | NT | NT | NT | NT | NT | NT |
| RPMI/M199 | + | + | NT | NT | NT | NT | NT | NT |
| HBSS | +++ | ++++ | +++ | +++ | +++ | + | + | NT |
| GALA | ++++ | ++++ | ++++ | ++++ | ++++ | ++++ | ++++ | ++++ |

Scoring system:
+ 0-25% viable,
++ 26-50% viable,
+++ 51-75% viable,
++++ 76-100% viable.
Each viability score is the mean from at least two different patients.
HLS = heparin + lidocaine + saline,
Blood = blood with added heparin (50 Units/mL),
RPMI/M199 = culture media in 1:1 ratio,
HBSS = Hanks' balanced salt solution,
GALA = HBSS with ascorbic acid, glutathione, L-arginine, and heparin.
NT = not tested secondary to lack of predicted viability.

For NO measurements, typically the lumenal endothelium was identified in a field of view at 40× magnification after XYZ scanning. Bradykinin stimulated egos activity in the endothelium was measured by quantitating the increase in DAF fluorescence due to generation of NO over 20 min at 21° C. More particularly, the generation of endothelial NO intact vessels was determined using the NO indicator dye DAF-2. In this method, vessel segments were loaded with the membrane permeate diacetate form of 4,5-diaminofluorescein, which is cleaved by cellular esterases to a membrane impermeant form. This dye then combines with intracellularly generated NO to yield the brightly fluorescent triazolofluorescein derivative. Vessel segments were incubated with 15 μM DAF-2/DA in HBSS for 60 minutes at 37° C. After the incubation, vessels were washed with three changes of HBSS to remove the excess dye. The chamber bearing the segment in 100 μl HBSS was mounted on the microscope and imaged as described below. The vessel egos activity was stimulated by gently adding 5 μl of a 200 μM stock solution of bradykinin in HBSS, to a final concentration of 10 μM to the chamber. The specificity of egos activity in the vessels was measured in the presence or absence of $N^w$-nitro-L-arginine (L-NNA). Vessel segments were pre-incubated with 100 μM of L-NNA in 1.5 ml of HBSS for 30 min at 37° C., prior to further incubation with DAF. Basal activity of egos was measured in absence of bradykinin stimulation, by sham incubating the vessel in HBSS for similar period. The Vessel segments were imaged and the nitric oxide generation was measured by quantitative epifluorescence multi-photon microscopy as described below. Temporal changes in DAF-2 fluorescence were recorded in real time before, and 10 minutes and 20 minutes after bradykinin treatment. Boundaries were drawn along the endothelium in 2-3 regions of the vessel lumen and changes in the integrated fluorescence intensity within each boundary was monitored over time and integrated over all pixels within the boundary for that region using BioRad Laser Sharp software. Because the size and shape of the regions varied with the source and size of the vessel, and the endothelial layer, and to eliminate effects due to variation in DAF dye loading, fluorescence intensities from each image were normalized by those from a reference image recorded prior to the bradykinin treatment for each experiment. The data is expressed as temporal change in relative fluorescence intensity, and is the average of at least three blinded experiments performed on different days. HLS, blood, and culture media provided very poor protection to the endothelial cells resulting in low cell viability. HBSS was found to maintain cell viability up to 3 hours of storage, but was inadequate after that point. Again, in sharp contrast to the other solutions, GALA was able to maintain cell viability even after 1440 minutes (24 hours) of storage.

Figure 3:
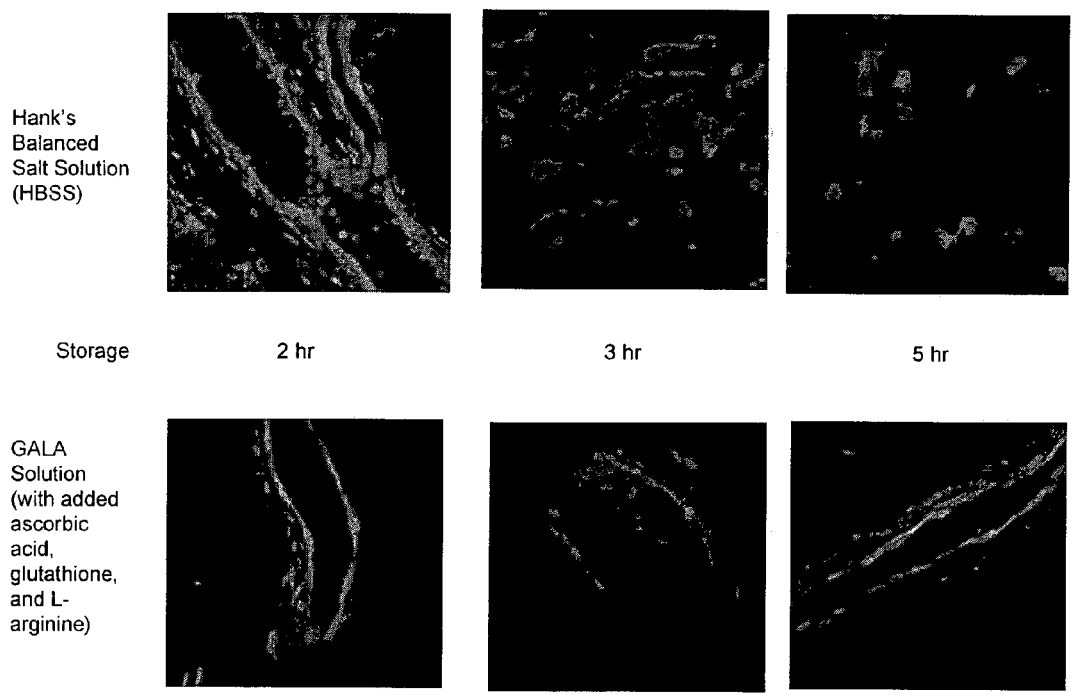
FIG. 3 shows a comparison of cell viability of human saphenous veins stored in HBSS verses GALA solution.
Figure 4:
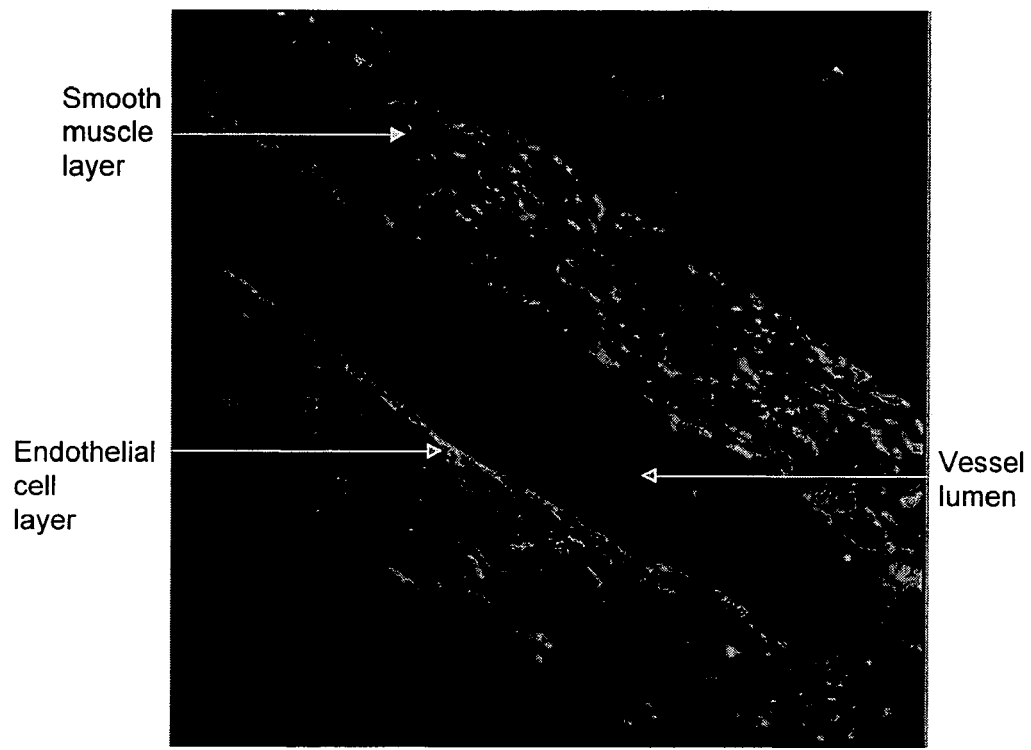
FIG. 4 shows cell viability of a human saphenous vein following 24 hours of storage in GALA solution.

FIG. 3 depicts a comparison between HBSS and GALA solution following 5 hours of storage. At two hours, no difference in cell viability can be seen. However after three hours, a marked contrast exist in terms of cell protection between these solutions. Note in the HBSS images following 3 and 5 hours of storage, how the endothelial layer is completely non-viable and has lost its architecture. The images for the GALA solution not only show near-total cell viability, but also demonstrate preservation of the cellular architecture. In FIG. 4, the near-total preservation of the vein is noted after 24 hours of storage in GALA solution.

EXAMPLE 3

Figure 5:
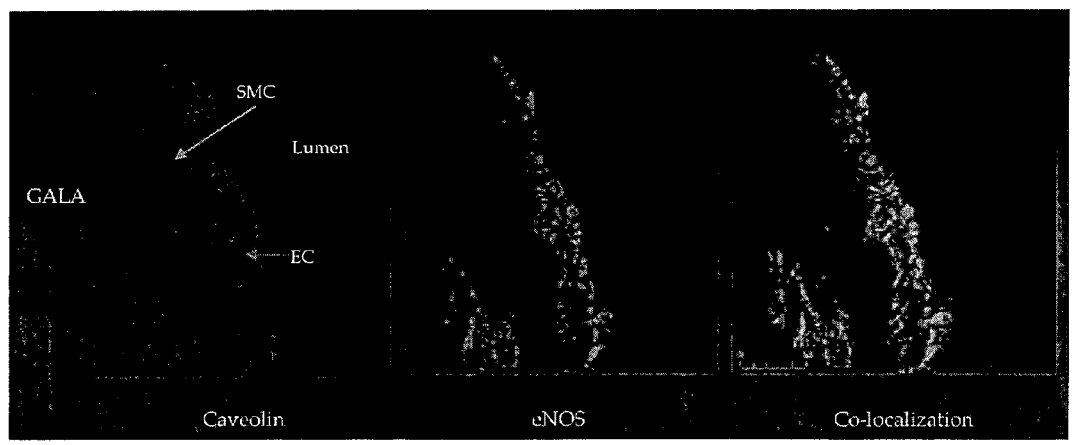
FIG. 5 shows immunofluorescence labeling of SVG stored in GALA and HLS for 3 hours.

In order to elucidate the molecular mechanisms that are affected by the storage conditions, the vessel conduits were stored in HLS and GALA for 1-3 hours. Segments were then labeled with anti caveolin and anti egos antibodies and appropriate fluorescence tagged secondary antibodies. The immunofluorescently labeled vessels were imaged using the multi-photon imaging system. As shown in FIG. 5, both the caveolin and egos were robustly labeled with the antibodies in vessels stored in GALA for 3 hours. Furthermore, caveolin and egos colocalized on the plasma membrane of the EC. In contrast, these molecules were poorly labeled and did not colocalize in vessels stored in HLS. These results clearly demonstrate that GALA protected vessel endothelium at the molecular level, as cavolin and egos were maintained at their respective functional location seen in normal vessels. In contrast, HLS translocated these molecules to the nonfunctional interior regions of the EC and hence did not label well. It is also possible that HLS caused sloughing of the EC layer and poor labeling of these molecules. Thus long term protective effect of GALA is clearly evident.

EXAMPLE 4

Figure 6:
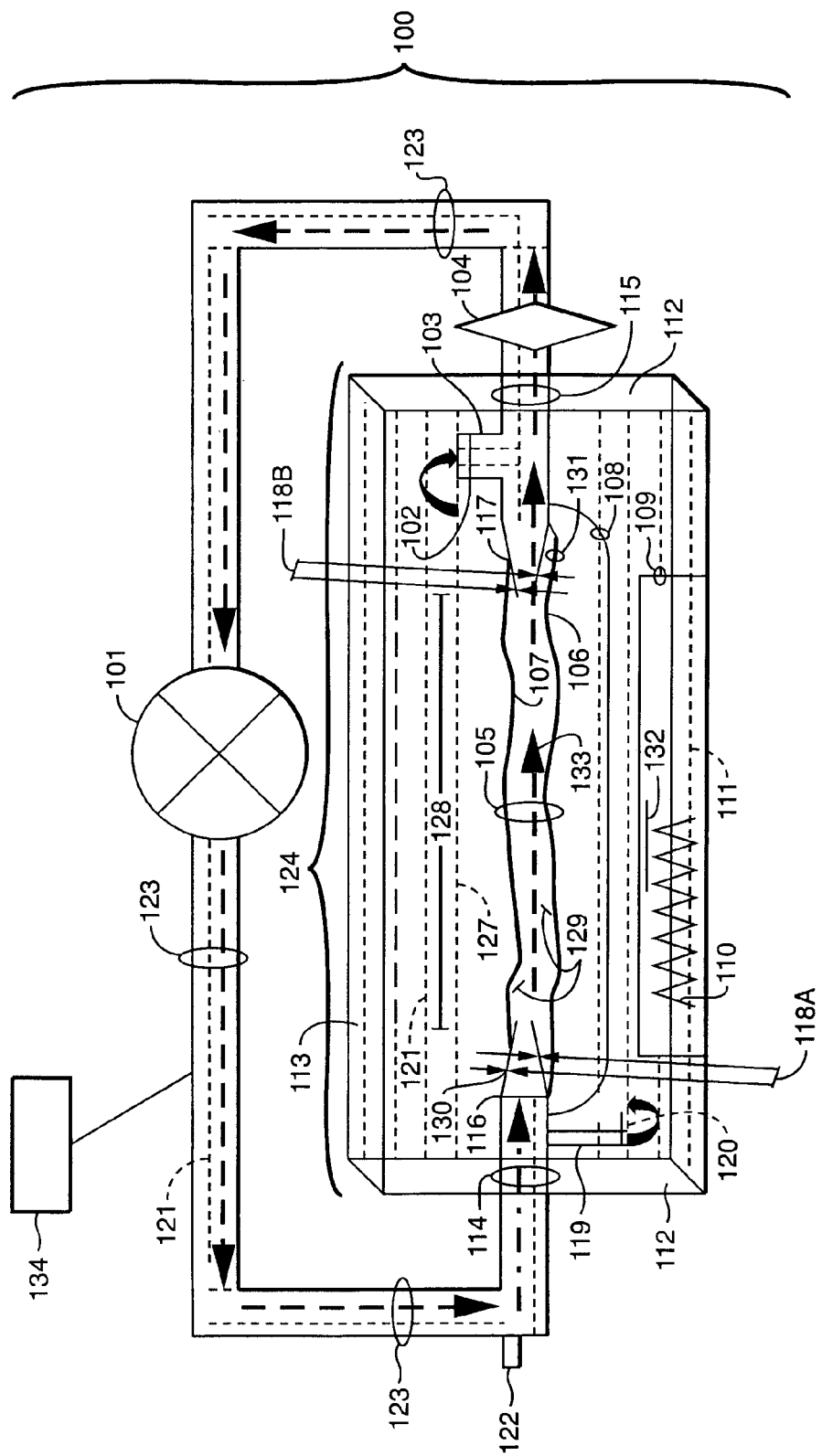
FIG. 6 shows one embodiment of a perfusion device contemplated by the present invention.

One embodiment of a perfusion device is set out in FIG. 6. This perfusion device 100 comprises a tissue perfusion chamber 124 in fluidic communication with a perfusion circuit 123 that is operably linked to a pump 101 wherein said pump is regulated by a pressure transducer 104 integrated into said perfusion circuit 123.

The perfusion chamber 124 defines a reservoir which may confine fluid, comprising a chamber floor 111, by a chamber side 112, with a removable chamber lid 113, said chamber side 112 having a first inlet port 114 and a second outlet port 115. Said first inlet port 114 provides an aperature through which the perfusion circuit 123 is operably linked with an adjustable serrated inlet nozzle 116 such that an efflux port 119, operably connected to a efflux port valve 120 (in fluidic communication with the interior 127 of said tissue perfusion chamber 124), is disposed between said inlet port 114 and said serrated inlet nozzle 116.

Said second outlet port 115 provides an aperature through which the perfusion circuit 123 is operably linked with an adjustable serrated outlet nozzle 117 such that an uptake port 102 (said uptake port having a lumen greater than said efflux port) is operably connected to a uptake port valve 103 (in fluidic communication with the interior 127 of said tissue perfusion chamber 124), is disposed between said uptake port 114 and said serrated outlet nozzle 117.

The present device provides for the connection of a blood vessel 105 wherein the first end 130 of a blood vessel 105 is fitted over the adjustable serrated inlet valve 116 such that said first vessel end 130 is secured about said adjustable serrated valve 116 with a clamping means 118a and said second blood vessel end 131 of blood vessel 105 is fitted over the adjustable serrated outlet valve 117 wherein said second vessel end 131 is secured about said adjustable serrated outlet valve 117 with a clamping means 118b. The blood vessel in the present example is a saphenous vein having intra luminal valves 129, associated with the tunica intima 107, that are oriented such that said valves 129 remain open when the physiological solution 121 is circulated, in the direction indicated by the arrow 133 from the adjustable serrated inlet nozzle 116 to the adjustable serrated outlet nozzle 117.

Furthermore, the blood vessel 105 may be supported according to a variety of means including, but not limited to, a mesh hammock 108 suspended between said adjustable serrated inlet nozzle 116 and said adjustable serrated outlet nozzle 117; a mesh table 109 contacted to the chamber floor 111; and convolutions 110 pre-formed in the chamber floor which form a corrugated plane below the blood vessel 105.

The physiological solution 121 may be added to the present device according to a variety of means. The chamber lid 113 may be removed and the solution may be poured directly into the chamber. A reservoir of physiological solution 121 may be placed in fluidic communication with the perfusion circuit 123 such that the pump 101 will draw physiological solution 121 from the reservoir 134 into the perfusion device 101. In the alternative powdered, lyophilized, or tableted physiological components (including GALA) may be pre-measured into the interior of the perfusion chamber such that a physiological solution is created upon the addition of a given volume of water. Finally, the injection port 122 provides direct access to the chamber interior such that the blood vessel may be exposed to various compounds.

EXAMPLE 5

Figure 7:
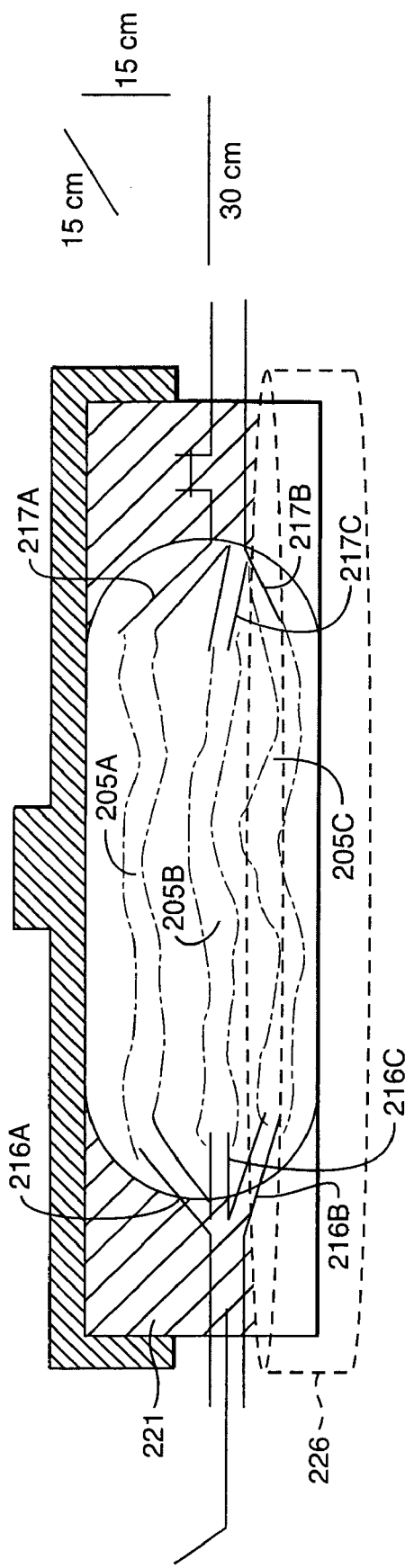
FIG. 7 shows an alternative configuration of the perfusion device depicted in FIG. 6.

The device described in Example 4, and set out in FIG. 6, may be reconfigured according to a variety of modification including, but not limited to, the following alterations. FIG. 7 shows how the inlet 116 and outlet nozzles 117 (as shown in FIG. 6) may be divided into two or more manifolds, thereby forming a plurality of inlet nozzles (e.g., 216a, 216b, and 216c) and outlet nozzles (e.g. 217a, 217b, and 217c) such that a plurality of vessels (e.g. 205a, 205b, and 205c) may be perfused simultaneously. In addition, the perfusion chamber 224 may be placed on a temperature control unit 226 which allows for the heating or cooling of the circulating physiological solution 221.

EXAMPLE 6

In a preferred embodiment, the apparatus described in FIG. 6 and FIG. 7 consists of a sterile, self-contained, disposable tissue perfusion chamber 124 of surgically compatible material (plastic) containing the GALA vessel preservation solution (e.g. a physiological solution). The entire unit can be fitted on a tray on top of a pushcart in the operating room. Specifically, a 30 cm×15 cm×15 cm disposable plastic perfusion chamber 124 with a lid 113 and an independent temperature control element 126 to control the temperature of the system. Inlet 116 and outlet 117 ports that are connected to flexible tubing is threaded into a variety of pumps 101 (e.g. pulsatile, intermittent, reversible, able to generate sine and/or square waves).

A sterile inert screen/mesh/harnmock 108 (nylon/nitrocellulose) suspended from the inlet/outlet ports support/suspend attached human blood vessels 105. A traumatic vascular clamps 118a are used attach the vessel(s) 105 to the nozzle(s) 116 and vascular clamps 118b are used attach the vessel(s) 105 to the nozzle(s) 117. A univalve (unidirectional) injection port 122 is disposed in the flexible tubing 123 for injecting pharmacological agents.

A pressure transducer 104 attached to the outlet port and connected to the pump. GALA is pumped through the system at a desired pressure regulated by an electronic feedback control loop with the pressure transducer. The chamber 124 and the tubing 123 are filled with GALA solution. Air pockets are thus avoided.

A larger bore uptake port 104 (on the outlet) and a smaller bore GALA efflux port 119 (on the inlet) provide continuous circulation of fresh GALA from the chamber through the vessel. The bore size differential create enough turbulence in the chamber so that the suspended vessels can be continually levaged with GALA to remove any boundary layer free radicals, and metabolites on the external surface of the vessel (e.g. the tunica adventitia 106).

EXAMPLE 7

A surgeon harvests a saphenous vein from the leg of an anesthetized patient and divides the vein into segments of desired length. The segments are transferred to the perfusion chamber 124, suspended on the mesh hammock 108 submerged in GALA solution, and are clamped onto the inlet nozzles 116 with a traumatic tissue clamps. The pump 101 is run for a short time to remove any air trapped in the vessel. The other ends of the vessel are clamped on outlet nozzles 117. The vessel is then perfused with GALA by continuously cycling the pump 101. Any leaking branches on the blood vessel 105 can be tied off.

In a preferred embodiment, the pump output is adjusted to maintain optimal intra-lumenal pressure (generally 90-120 mm Hg). In addition, the uptake port valve 102 and efflux port valve 120 may be regulated to adjust the intra-lumenal pressure for a constant pump output rate. The temperature of the circulating physiological solution 121 may be regulated by the temperature control unit. The vessels are perfused untill anastomosis. The perfusion activates flow induced release of nitric oxide and prostacychn from the endothelial cells, and thus help dilate the vessel and also maintain its patency during storage. Further high-pressure dilation of the vessel is not required for anastomosis. The veins are also preconditioned for arterial flow and pressure. Perfusion mediated inhibition of release of vasoconstrictors and neutralization of free radicals by the GALA protects the vessel in storage during CABG surgery.

EXAMPLE 8

Distension of vein grafts prior to anastomosis is a common practice in CABG surgery. This process allows the surgeon to check for the patency of the graft, as well as leakage. However, pressurization of the vessel above physiological pressures with saline solutions causes a considerable amount of damage to the endothelium, intima and the media of the vessel. Using calcein-ethidium homodimer assays and multiphoton microscopy the detrimental effects of distension on vessel structure and function are easily observed. The convoluted viable endothelial regions of the freshly excised saphenous vein, identified by the green living cell fluorescence, were denuded and structurally damaged due to distension prior to anastomosis apparent from the considerable amount of red fluorescence observed in the intima and media of these distended vessels. Data not shown.

This complication is circumvented by physiological preconditioning and distension, provided by the perfusion techniques of the present invention, that maintains structure, function, and patency of blood vessels (especially saphenous veins) in storage during CABG surgery. In contrast to the conventionally distended saphenous vein (300 mm Hg pressure), a robust green fluorescence of living cells was observed in the endothelial region of saphenous vein distended by using the newly developed perfusion system (90 mm Hg pressure).

EXAMPLE 9

Figure 8:
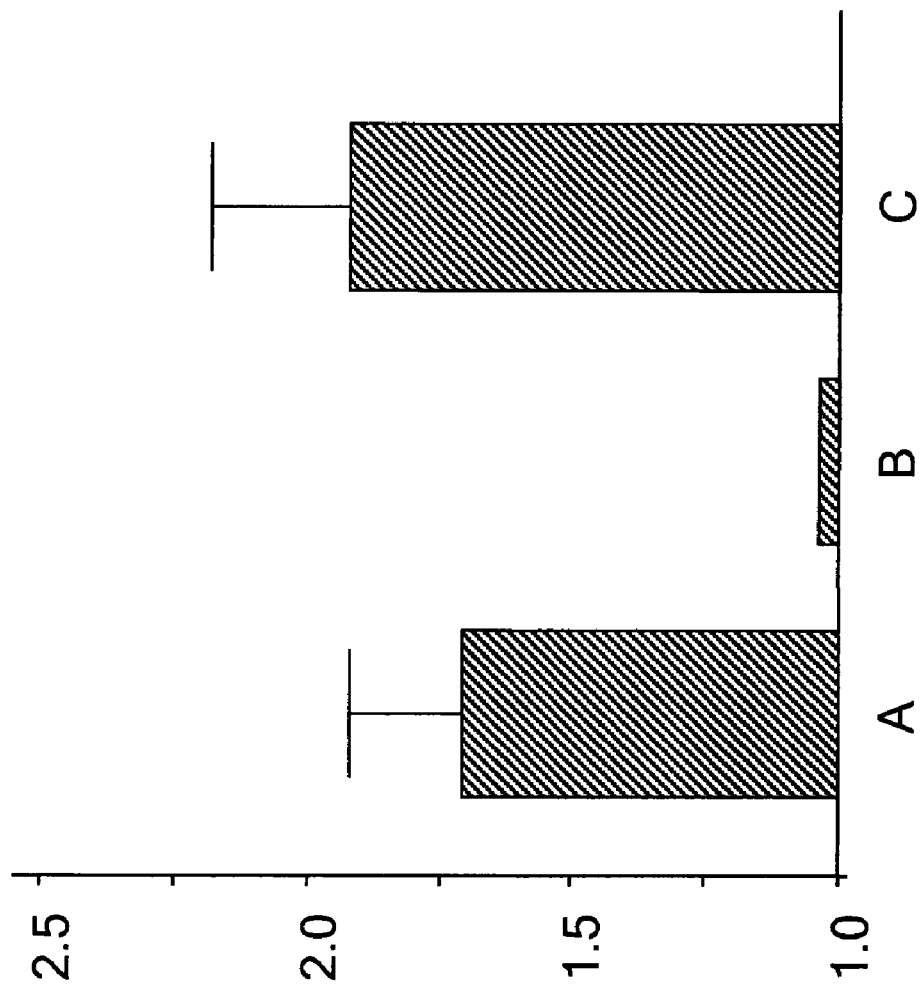
FIG. 8 is a bar graph showing data comparing physiological function between human saphenous vein grafts distended according to methods described in the prior art and veins distended according to perfusion methods of the present invention (as compared to undistended control).

Conventional blood vessel physiological distension techniques adversely effect endothelial function in these vessels. Specifically, generation of nitric oxide was completely attenuated in the conventionally distended vessels as seen in bar graph "B" of FIG. 8 (expressed in terms of arbitrary units of normalized fluorescence activity on the y-axis). In contrast, a robust activation of egos and production of nitric oxide was observed in physiologically distended vessels using the perfusion system described in the present invention as seen in bar graph "C" of FIG. 8 (once again, expressed in terms of arbitrary units of normalized fluorescence activity on the y-axis; with bar graph A of FIG. 8 serving as an undistended control).

In view of these data, the perfusion methods of the present invention maintain the structural and functional viability of blood vessels (especially saphenous veins) used as bypass thereby promoting long-term patency of the grafts.

It is evident from the above that the present invention provides a novel and nonobvious composition and methods for the preservation of tissues and organs both ex vivo and in situ.

The invention claimed is:

1. A device comprising, an incomplete, hollow circuit defining a liquid flow path in fluidic communication with a chamber comprising an inlet port and an outlet port, said incomplete circuit comprising a pump operably linked to a pressure transducer, said circuit terminating at first and second attachment points, wherein said circuit comprises an efflux port disposed between said inlet port and said first attachment point and an uptake port disposed between said outlet port and said second attachment point, wherein the bore of said uptake port bore is larger than the bore of said efflux port thereby resulting in a bore size differential creating enough turbulence to continuously lavage a blood vessel, such that attachment of a first end of said blood vessel to said first attachment point and a second end of said blood vessel to said second attachment point generates a complete, hollow circuit defining a liquid flow path.

2. The device of claim 1, wherein said first attachment point comprises a serrated nozzle.

3. The device of claim 1, wherein second attachment point comprises an adjustable serrated nozzle.

4. The device of claim 1, wherein said chamber is sterile.

5. The device of claim 1, wherein said chamber is disposable.

6. The device of claim 1, wherein said incomplete, hollow circuit comprises tubing, said tubing terminating inside said chamber at said first and second attachment points.

7. The device of claim 1, wherein said tubing is in fluidic communication with a reservoir.

8. A method for perfusion, comprising:
a) providing i) a device comprising, an incomplete, hollow circuit defining a liquid flow path in fluidic communication with a chamber comprising an inlet port and an outlet port, said incomplete circuit comprising a pump operably linked to a pressure transducer, said circuit terminating at first and second attachment points, wherein said circuit comprises an efflux port disposed between said inlet port and said first attachment point and an uptake port disposed between said outlet port and said second attachment point, wherein the bore of said uptake port bore is larger than the bore of said efflux port thereby resulting in a bore size differential creating enough turbulence to continuously lavage a blood vessel; and ii) a segment of a blood vessel, said blood vessel having a first end and a second end;
b) attaching, in any order, said first end of said segment to said first attachment point and said second end of said segment to said second attachment point, under conditions such that a complete, hollow circuit defining a liquid flow path is produced; and
c) circulating an aqueous solution in said hollow circuit.

9. The method of claim 8, wherein said aqueous solution comprises an antioxidant and L-arginine.

10. The method of claim 9, wherein said aqueous solution further comprises an anticoagulant.

11. The method of claim 10, further comprising a cellular reducing agent.

12. The method of claim 8, wherein said blood vessel is an isolated vein.

13. The method of claim 12, wherein said vein is a saphenous vein.

* * * * *

UNITED STATES PATENT AND TRADEMARK OFFICE
CERTIFICATE OF CORRECTION

PATENT NO. : 7,611,830 B2
APPLICATION NO. : 10/257176
DATED : November 3, 2009
INVENTOR(S) : Thatte et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1501 days.

Signed and Sealed this

Twelfth Day of October, 2010

David J. Kappos
*Director of the United States Patent and Trademark Office*